US010556093B2

(12) United States Patent
Konstantarakis et al.

(10) Patent No.: US 10,556,093 B2
(45) Date of Patent: Feb. 11, 2020

(54) MEDICAL DEVICES, DRESSINGS, AND METHODS FOR CLOSING OPENINGS IN TISSUE

(71) Applicant: Confluence LLC, Laguna Niguel, CA (US)

(72) Inventors: Joseph Michael Konstantarakis, Laguna Niguel, CA (US); Peter Karl Schollenberger, San Clemente, CA (US); Scott Clinton Anderson, Sunnyvale, CA (US)

(73) Assignee: Confluence, LLC, Laguna Niguel, CA (US)

( * ) Notice: Subject to any disclaimer, the term of this patent is extended or adjusted under 35 U.S.C. 154(b) by 243 days.

(21) Appl. No.: 15/101,580

(22) PCT Filed: Dec. 31, 2014

(86) PCT No.: PCT/US2014/073057
§ 371 (c)(1),
(2) Date: Jun. 3, 2016

(87) PCT Pub. No.: WO2015/103423
PCT Pub. Date: Jul. 9, 2015

(65) Prior Publication Data
US 2016/0303350 A1    Oct. 20, 2016

Related U.S. Application Data

(60) Provisional application No. 61/992,812, filed on May 13, 2014, provisional application No. 61/922,398, filed on Dec. 31, 2013.

(51) Int. Cl.
A61M 25/02        (2006.01)
A61M 39/02        (2006.01)
(Continued)

(52) U.S. Cl.
CPC ......... *A61M 25/02* (2013.01); *A61B 17/0057* (2013.01); *A61M 39/0247* (2013.01);
(Continued)

(58) Field of Classification Search
CPC .. A61M 25/02; A61M 39/06; A61M 39/0613; A61M 39/0247;
(Continued)

(56) References Cited

U.S. PATENT DOCUMENTS 1,969,188 A    8/1934 Spicer
3,487,837 A    1/1970 Petersen
(Continued)

FOREIGN PATENT DOCUMENTS

AU    2009203014 A1    3/2010

OTHER PUBLICATIONS

International Search Report and Written Opinion for counterpart International Application No. PCT/US2014/073057; dated Apr. 6, 2015, 12 pages.

*Primary Examiner* — Kevin C Sirmons
*Assistant Examiner* — Tezita Z Watts
(74) *Attorney, Agent, or Firm* — Perkins Coie LLP

(57) ABSTRACT

Medical devices and methods for controlling the flow of fluid from wounds are disclosed herein. The medical device can have an adhesive pad defining a catheter-receiving opening, a flexible elongate tensioner, and a tensioner retainer. The tensioner retainer is configured to hold the flexible elongate tensioner such that the adhesive pad applies sufficient pressure to a subject's skin to press the subject's tissue toward a catheter when the catheter is positioned in the catheter-receiving opening and the adhesive pad is adhered to the subject's skin.

23 Claims, 12 Drawing Sheets

US 10,556,093 B2
Page 2

(51) Int. Cl.
*A61B 17/00* (2006.01)
*A61M 39/06* (2006.01)

(52) U.S. Cl.
CPC ............... *A61B 2017/00884* (2013.01); *A61B 2017/00951* (2013.01); *A61M 2025/024* (2013.01); *A61M 2025/0253* (2013.01); *A61M 2025/0273* (2013.01); *A61M 2039/027* (2013.01); *A61M 2039/0261* (2013.01); *A61M 2039/0673* (2013.01)

(58) Field of Classification Search
CPC .... A61M 2025/024; A61M 2025/0253; A61M 2025/0273; A61M 2039/0261; A61M 2039/0273; A61M 2039/0673; A61M 2025/0286; A61B 2017/00884; A61B 2017/00951
See application file for complete search history.

(56) References Cited

U.S. PATENT DOCUMENTS

| | | | |
|---|---|---|---|
| 3,971,384 A | 7/1976 | Hasson | |
| 4,221,215 A | 9/1980 | Mandelbaum | |
| 4,360,025 A | 11/1982 | Edwards | |
| 4,645,492 A | 2/1987 | Weeks | |
| 4,699,616 A | 10/1987 | Nowak et al. | |
| 4,706,661 A | 11/1987 | Barrett | |
| 4,865,026 A | 9/1989 | Barrett | |
| 4,874,380 A | 10/1989 | Hesketh | |
| 4,881,546 A | 11/1989 | Kaessmann | |
| 5,073,170 A | 12/1991 | Schneider | |
| 5,176,703 A | 1/1993 | Peterson | |
| 5,224,935 A | 7/1993 | Hollands | |
| 5,261,893 A | 11/1993 | Zamierowski | |
| 5,665,108 A | 9/1997 | Galindo | |
| 5,665,180 A | 9/1997 | Galindo | |
| 6,117,163 A * | 9/2000 | Bierman | A61M 25/02 24/16 R |
| 6,638,296 B2 | 10/2003 | Levinson | |
| 7,887,501 B2 | 2/2011 | Riordan et al. | |
| 7,972,362 B2 | 7/2011 | Wilke et al. | |
| 8,439,945 B2 | 5/2013 | Belson et al. | |
| 8,974,421 B1 * | 3/2015 | Khalaj | A61M 25/02 604/174 |
| 2002/0156495 A1 | 10/2002 | Brenneman et al. | |
| 2004/0204740 A1 | 10/2004 | Weiser | |
| 2006/0095008 A1 * | 5/2006 | Lampropoulos | A61M 25/02 604/174 |
| 2009/0234295 A1 * | 9/2009 | Lampropoulos | A61M 25/02 604/174 |
| 2009/0281503 A1 | 11/2009 | Lampropoulos et al. | |
| 2011/0118670 A1 * | 5/2011 | Kay | A61M 25/02 604/177 |
| 2013/0066365 A1 | 3/2013 | Belson et al. | |

* cited by examiner

MEDICAL DEVICES, DRESSINGS, AND METHODS FOR CLOSING OPENINGS IN TISSUE

CROSS-REFERENCE TO RELATED APPLICATIONS

The present application claims priority under 35 U.S.C. § 119(e) to U.S. Provisional Application Ser. No. 61/922,398, filed Dec. 31, 2013 and to U.S. Provisional Application Ser. No. 61/992,812, filed May 13, 2014, the disclosures of which are incorporated herein by reference in their entireties.

TECHNICAL FIELD

The present disclosure relates generally to medical devices and, more particularly, to adhesive devices, dressings, and methods for covering and/or closing openings in tissue, including openings through which catheters or other instruments pass in order to minimize/stop the flow of fluid through such openings.

BACKGROUND OF TECHNOLOGY

Catheters are often placed in patients for various reasons. Significant resources may be required to stem fluid flow (e.g., ongoing oozing/leaking of fluids, such as blood) around recently placed catheters, such as drainage catheters and vascular catheters. Upon catheter insertion, gauze is often placed directly on the catheter exit site and then manually compressed to stem bleeding. Unfortunately, manual compression often requires relatively long hold times, significant amounts of gauze, blood transfusions and infusions, and frequent gauze replacement. Additionally, it is difficult to manually apply consistent pressure suitable for promoting clotting without causing significant pain or discomfort.

When manual compression is not suitable for achieving clotting, invasive purse-string sutures are often used to close wounds. To place a purse-string suture, tissue surrounding the catheter exit site is prepped and draped sterilely. A needle and a needle driver are used to thread a continuous stitch repeatedly through the patient's skin until the stitch surrounds the catheter. Two ends of the stitch are pulled together to draw the patient's skin towards the catheter, and the ends can be tied together. After sufficient time has passed to allow clotting, the purse-string stitch can be cut using sterile scissors and removed from the patient. Unfortunately, purse-string procedures are time-consuming and performed by physicians or other highly trained practitioners (e.g., physician assistants). Additionally, purse-string sutures may be unsuitable for areas with cellulites, infection (e.g., bacterial infection), and/or bacteremia and also unsuitable for patients with diseases affecting circulation, such as peripheral vascular disease, diabetes, or other diseases that result in poor blood flow to the skin.

SUMMARY OF TECHNOLOGY

At least some embodiments are medical devices and methods for limiting, minimizing, or preventing the flow of fluid from openings (e.g., surgical or nonsurgical openings) in a subject's tissue. The devices can be noninvasive adhesive dressings configured to selectively increase or decrease pressure/force applied to the subject's tissue so as to at least partially close openings. In some embodiments, hemostasis or other desired results can be achieved by applying sufficient pressure/force to minimize, limit, or substantially prevent pericatheter leakage (e.g., oozing, bleeding, etc.). The devices can be used to avoid costly and complicated invasive procedures, as well as time-consuming manual compression procedures.

In some embodiments, a device is configured to provide cinching action for preventing ongoing leaking/oozing of fluids or other substances from an opening. The device includes an adhesive base, an access feature, and a through-hole. The adhesive base can be adhered to any surface. The access feature can be a slit through which a catheter, or other instrument, can pass to access the through-hole. The device, in some embodiments, includes one or more holders (e.g., rings, loops, or hooks) positioned about the through-hole and a flexible element (e.g., a suture, a string, a tether, a strap, a band, etc.). The flexible element can pass through the holders such that tensioning of the flexible element causes mechanical closing of the opening (e.g., a wound along the patient's skin). The device can include a releasable and reusable locking feature for maintaining tension in the flexible element. The device can also include one or more retainers configured to prevent or limit movement of another component, such as a line, a catheter, or an instrument, extending through the through-hole.

At least some embodiments are a device can include a conformable base, a locking mechanism, and a flexible tensioner. The conformable base can include an adhesive bandage, adhesive patch, or other flexible component capable of transmitting forces/pressure to a subject's body. The tensioner can be coupled to the conformable base and tensioned such that the base applies pressure/force to the subject. In one embodiment, the device can close an opening in the subject's skin. The locking mechanism can have an unlocked state for releasing the tensioner or reducing tension in the tensioner and a locked state for securely holding the tensioner to maintain tension.

In some embodiments, a noninvasive cinching device comprises a compliant adhesive pad defining a catheter-receiving opening, a flexible elongate tensioner, and a tensioner retainer. The tensioner is configured to be coupled to the compliant adhesive pad such that a tensioned section of the flexible elongate tensioner is spaced apart from and extends about the catheter-receiving opening. The tensioner retainer is configured to hold the flexible elongate tensioner such that the compliant adhesive pad applies sufficient pressure to a subject's skin to press the subject's tissue toward the catheter when the catheter is positioned in the catheter-receiving opening and the adhesive pad is adhered to the subject's skin. In some embodiments, the adhesive pad can include an adhesive bandage, an adhesive patch, or other flexible component capable of transmitting forces/pressure to a subject's body.

In some further embodiments, a noninvasive cinching device is configured to externally close an orifice (e.g., an incision, a wound, etc.) so as to prevent ongoing exuding of fluids from the orifice. The cinching device can include an adhesive base, an access feature, a flexible tensioner (e.g., an elastic string/strap or a non-elastic string/strap), and an opening (e.g., a through-hole). The base can include tensioner holders through which the flexible tensioner passes. In some embodiments, the base can comprise both adherent areas and non-adherent areas and can comprise, in whole or in part, cloth, plastic, foam, or other material that retains its integrity when centrally directed forces are applied during cinching. For example, the tensioner can be pulled to cause cinching in which most or all parts of the cinching device and the subject's surface to which the cinching device is attached are pulled towards the orifice positioned within or beneath the opening. Tension can be maintained by a locking feature. The locking feature may allow for various degrees of tension to be exerted on the cinching device, as well as the underlying surface to which the device is adhered.

The tensioner holders can be rings, loops, or hooks and can be located in a wide variety of arrangements. The holders can be spaced apart to increase or maximize the closing forces applied to the orifice in the subject tissue. In one embodiment, the holders are adhered, bonded, fused, or otherwise coupled to the adhesive base. In another embodiment, the holders are integrally formed with the base. Thus, the base and the holders can comprise the same material or different materials. The cinching device, in some embodiments, can have a retainer for holding medical devices (e.g., catheters, tubes, lines, or other instruments or other components, such as posts or anchors).

At least some embodiments are medical devices and methods for limiting, minimizing, or preventing the flow of fluid from openings (e.g., surgical or nonsurgical openings) not suitable purse-string sutures. The devices may be used at areas with cellulites, infection (e.g., bacterial infection), and/or bacteremia and also unsuitable for patients with diseases affecting circulation, such as peripheral vascular disease, diabetes, or other diseases that result in poor blood flow to the skin. The opening can be non-invasively closed to avoid complications associated with purse-string sutures.

BRIEF DESCRIPTION OF THE DRAWINGS

In the drawings, identical reference numbers identify similar elements or acts.

DETAILED DESCRIPTION

At least some embodiments of the medical devices disclosed herein can be noninvasive dressings positionable around/over an opening in tissue in order to minimize, inhibit, or prevent substances flowing through the opening. The devices can decrease resources (e.g., personnel time, materials, etc.) used to control or substantially eliminate bleeding/oozing/exuding fluids. The device can be applied by a wide range of individuals to quickly stem pericatheter leakage and/or promote wound healing. Although the devices are discussed in connection with promoting hemostasis, the devices and methods disclosed herein can be used in other applications to achieve different results. Exemplary devices and methods are discussed in connection with FIGS. 1-26.

Figure 1:
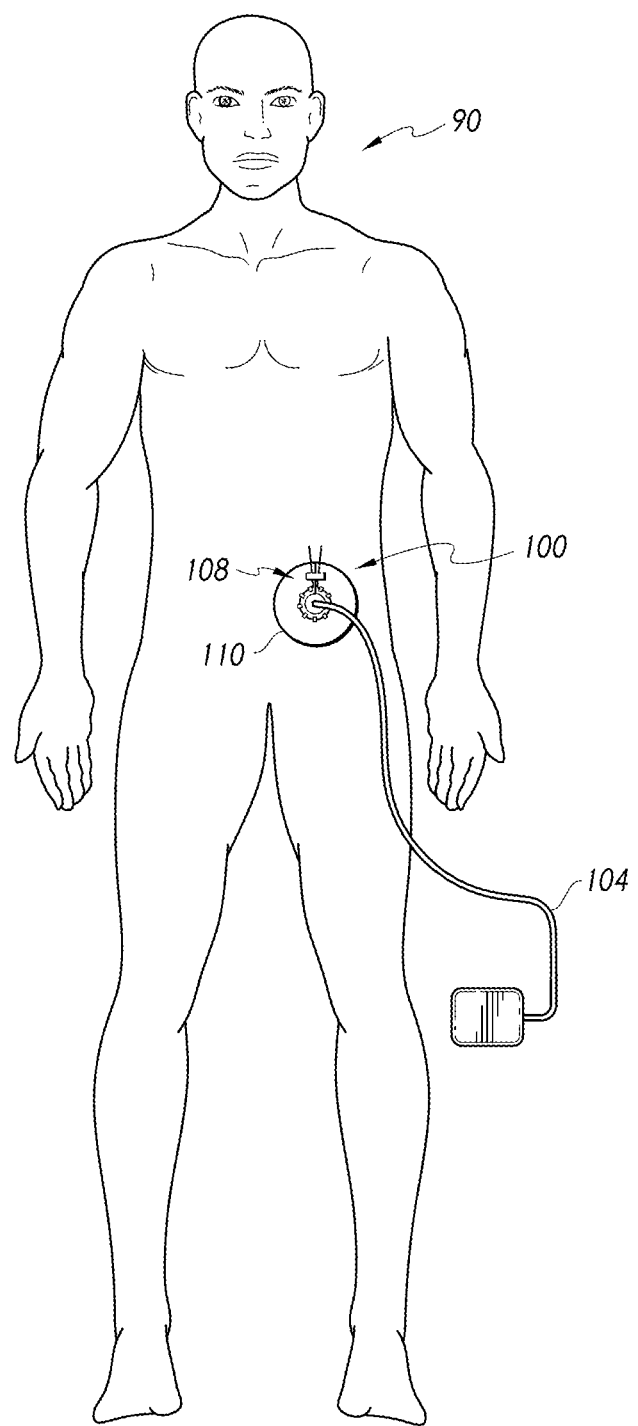
FIG. 1 is a plan view of a noninvasive cinching device applied to a subject in accordance with an embodiment of the technology.

FIG. 1 is a schematic view of a human subject 90 and a noninvasive cinching device 100 ("device 100") in accordance with an embodiment of the technology. The device 100 can be adhered to the subject 90 before, during, or most typically after the placement of a medical device 104 (e.g., a catheter) and can push tissue toward the device 104 to inhibit, limit, or substantially prevent wound exudate at an opening from which the device 104 exits the subject 90. To stem bleeding, a sufficient amount of pressure (e.g., a hemostatic level of pressure) can be applied to the subject's tissue. For example, the device 104 can apply pressure greater than or equal to venous blood pressure in instances where venous catheter site bleeding is occurring, or the device 104 can apply pressure greater than or equal to systolic blood pressure where arterial catheter site bleeding is occurring. Because the device 100 is noninvasive, it can be applied to areas with cellulites, active infections, and/or bacteremia and can also be used on subjects with diseases affecting circulation, including diseases that result in poor vascular supply to the subject's skin.

Figure 2:
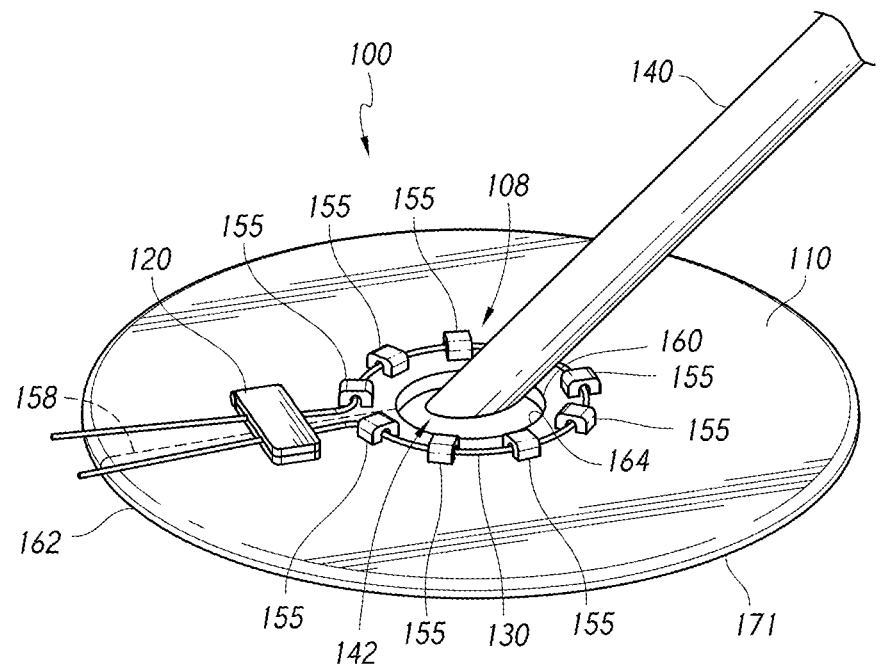
FIG. 2 is an isometric view of the cinching device of FIG. 1.
Figure 3:
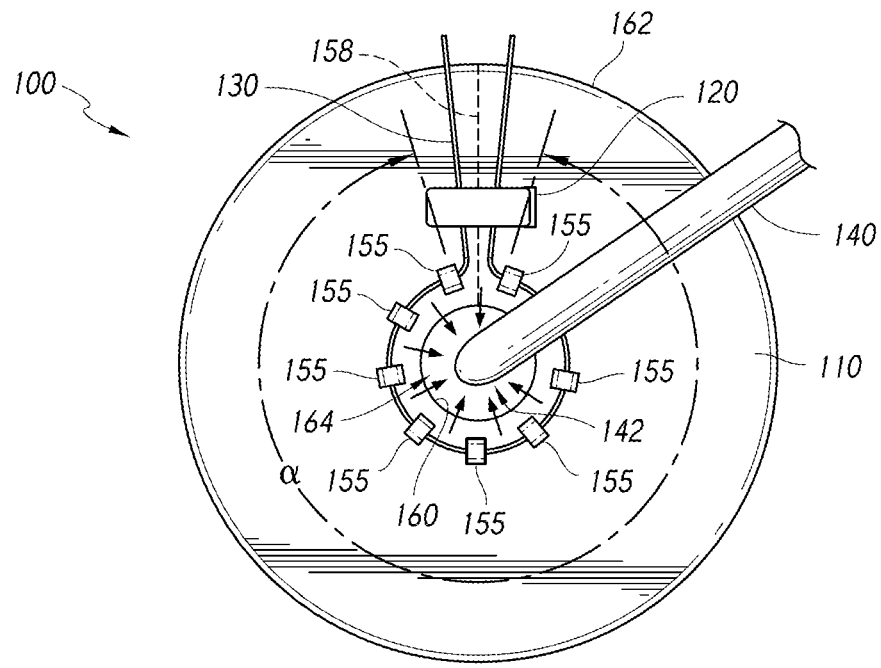
FIG. 3 is a plan view of the cinching device of FIG. 1.

FIGS. 2 and 3 are isometric and plan views, respectively, of the device 100 in accordance with an embodiment of the technology. Referring now to FIG. 2, the device 100 can include a cinching assembly 108 and a conformable base 110. The cinching assembly 108 can be used to repeatedly cinch and un-cinch and can include holders 155, an elongate flexible tensioner 130 ("tensioner 130"), and a tensioner retainer in the form of a locking mechanism 120. A tensioned section of the tensioner 130 can be spaced apart from and extend about a catheter-receiving opening 160. In some embodiments, the tensioned section can extend along a desired path (e.g., a generally circular path, an elliptical path, etc.) to provide forces (e.g., generally uniform radially forces) such that the base 110 exerts inwardly directed pressure on the underlying skin. By adjusting tension in the tensioner 130, the forces/pressure can be increased to minimize, limit, or substantially prevent pericatheter leakage, and the forces/pressure can be decreased to reduce pulling on the skin for enhanced comfort. The holders 155 can be in a circular arrangement (shown in FIGS. 2 and 3), elliptical arrangement, or other suitable arrangement and can be evenly or unevenly spaced apart from one another. The holders 155 can be eyelets, loops, slits in the base 110, or other features for holding the tensioner 130.

The tensioner 130 can include, without limitation, one or more sutures, tethers (e.g., string), wires, cables, and/or elongate flexible devices made of flexible or non-flexible material with sufficient tensile strength for providing a desired force. The tensioner 130 may be marked or labeled with numbers or other indicia (e.g., colored marks or bands for convenient visual identification) so as to allow measurable and reproducible tensioning. In one embodiment, a device operator can pull the tensioner 130 until the desired markings are placed in the locking mechanism 120 to provide a desired force.

The base 110 can be a compliant adhesive pad with a monolayer or multilayer construction and can comprise, in whole or in part, one or more conformable materials, such as foam, plastic, cloth, rubber, or other synthetic or natural cushioning materials that may be safely or comfortably applied to skin or other underlying tissue. A bottom surface 171 of the base 110 can comprise one or more adhesives that may strongly adhere to the subject's skin. In some embodiments, the adhesive may be dissolved using a solvent to allow for convenient device removal. Other types of adhesives can be used to allow for convenient device removal. The entire surface 171 can be defined by a uniform or non-uniform adhesive coating. Non-uniform adhesive coatings can have variable thicknesses, different adhesives at different locations, etc. whereas uniform coatings can have constant thicknesses, a single adhesive, etc. In some embodiments, the adhesive is applied to a portion, or selected portions, of the surface 171. The pattern and location of the adhesive can be selected based on, for example, the application site and desired forces to be applied to the subject. The base 110 may also comprise transparent material to allow for viewing through the device 100. For example, the transparent material can be partially or completely transparent to allow for direct viewing of tissue underlying the base 110. Additionally, the material of the base 110 proximate the opening 160 can comprise, for example, one or more antimicrobial agents for preventing infection and/or hemostatic agents for further preventing bleeding at or near the opening in the subject's tissue.

The base 110 can include one or more comfort features comprising compliant material(s) positioned to minimize, limit, or substantially prevent discomfort before, during, and/or after cinching. In one embodiment, the comfort features are anti-pinch features configured to limit or prevent pinching of skin between medical devices (e.g., medical device 104 of FIG. 1 or medical device 140 of FIGS. 2 and 3) and the device 100. In one embodiment, the comfort feature can be soft cushion material located at the undersurface of the device 100 or within layers of the base 110 and may protrude into the opening 160. The cushion material may include, but is not limited to, compliant substances that inhibit or prevent infection and/or bacterial growth, promote coagulation, absorb fluid, promote dryness of skin, adhere, and/or provide any other desired functionality. For example, the cushion material may comprise a soft absorbent foam material.

Referring now to FIG. 3, the opening 160 can be a generally round opening with a diameter in a range of about 4 mm to about 10 mm, about 2 mm to about 12 mm, or about 6 mm to about 15 mm and can be positioned in the center of the base 110. The opening 160 can have other dimensions and can be polygonal shaped and located off-center. In yet other embodiments, the opening 160 can be in the form of one or more slits or other types of apertures through which the device 104 can pass. The tensioned section of the tensioner 130 can encircle most of the opening 160. For example, the tensioned section can extend circumferentially about the opening 160 an angle α that can be equal to or greater than about 180 degrees. In some embodiments, the angle α is about 270 degrees to about 360 degrees, about 300 degrees to about 360 degrees, or about 330 degrees to about 360 degrees. To provide generally uniform inward pressure about the circumference of the device 104, the angle α can be equal to or greater than about 330 degrees. Other angles α can be used depending on the desired applied forces/pressure.

An access feature 158 (illustrated in dashed line) extends between outer and inner edges 162, 164 (See FIG. 2) of the base 110 and can be a slit. The locking mechanism 120 can be a clamp, a clip, or other feature capable holding the tensioner 130 and can be permanently or releasably coupled to the base 110. The locking mechanism 120 can have an unlocked state for adjusting the tension in the tensioner 130 and a locked state for maintaining the tension in the tensioner 130. Exemplary locking mechanisms are discussed in connection with FIGS. 9-16.

FIGS. 4-7 show one method of applying the device 100 to the subject.

Generally, the base 110 is adhered to the subject's skin such that the base 110 surrounds the device 104. The tensioner 130 is tensioned to pull the base 110 and the subject's skin towards the device 104. By providing cinching action, costs and/or time associate with intensive purse-string suture placement can be avoided. Additionally, the device 100 can be quickly applied by a wide range of individuals while avoiding lengthy typical holding/pressing times. Physicians, nurses, and other personnel are thus freed to perform other activities. The device 100 and methods of using the same are discussed in detail in connection with FIGS. 4-7.

Figure 4:
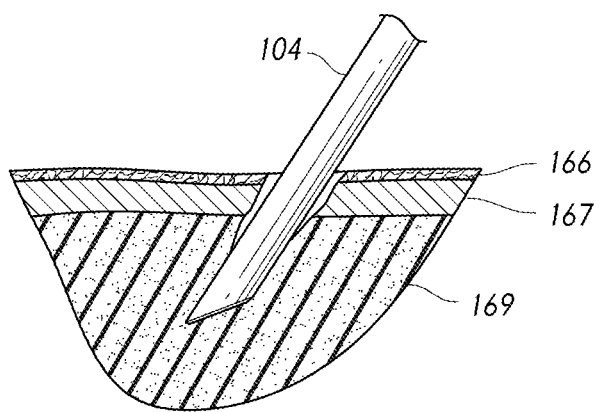
FIGS. 4-7 show one method of applying a noninvasive cinching device in accordance with an embodiment of the technology.

FIG. 4 shows the medical device 104 positioned in the subject. The device 104 can be a vascular catheter (e.g., a percutaneous venous or an arterial catheter), tunneled catheters, an indwelling catheter (e.g., an infusion catheter), a surgical drainage catheter, or other type of catheter extending through, for example, the epidermis 166, dermis 167, and/or subcutaneous tissue 169. The device 100 can be removed from sterilized packaging and a liner can be removed from the adhesive surface 171 (FIG. 2).

Figure 5:
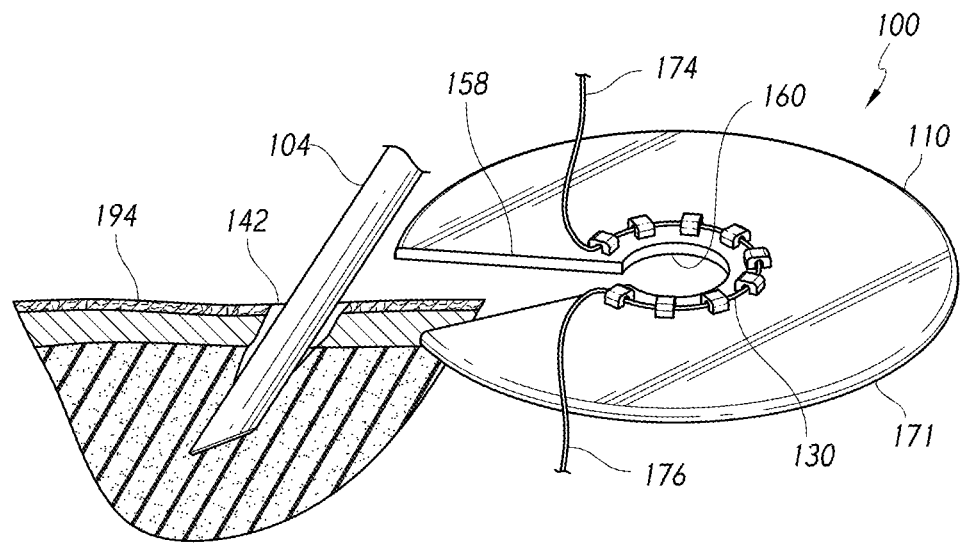

FIG. 5 shows the base 110 after the access feature 158 has been opened by, for example, separating the base 110 along a preformed score line, a tear line, a preferentially weakened feature, or the like. In other embodiments, scissors or other cutting instrument can be used to form the access feature 158. After the medical device 104 has passed through the access feature 158 and the base 110 has been aligned with the exit site or gap 142, the adhesive surface 171 can be placed onto the subject's skin 194. For example, the base 110 can be manually pressed against the subject's skin 194.

Figure 6:
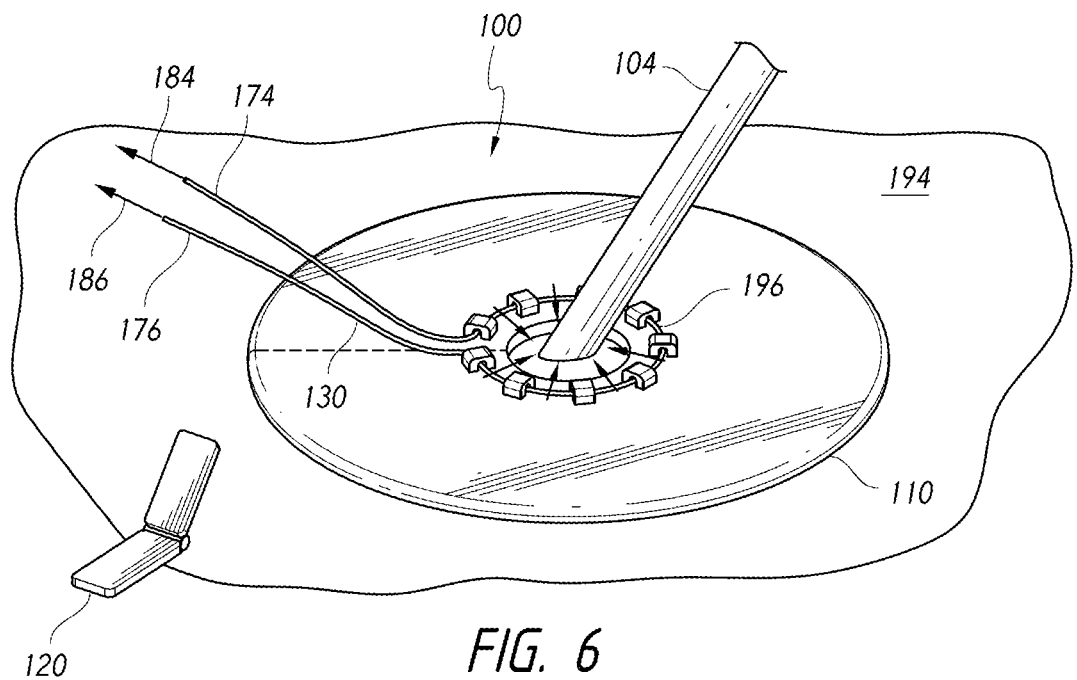

FIG. 6 shows the base 110 after it has been adhered to the subject's skin 194. The ends 174, 176 can be pulled (indicated by arrows 184, 186) to tension the section 196 of the tensioner 130 encircling the device 104. The tension can be increased or decreased to increase or decrease the closing pressure/force applied to the subject's skin 194. In some procedures, a user can manually apply pressure (e.g., by pressing down on the base 110) to keep the base 110 securely coupled to the subject's skin 194 during cinching. After the ends 174, 176 are placed in the open locking mechanism 120, the locking mechanism 120 can be moved from the open configuration (FIG. 6) to the closed configuration (FIG. 7) to securely hold the ends 174, 176. Adhesives, a coupler, or hook and loop type fastener, etc. can be used to couple the locking mechanism 120 to the base 110 before, during, or after the locking mechanism 120 is closed.

Figure 7:
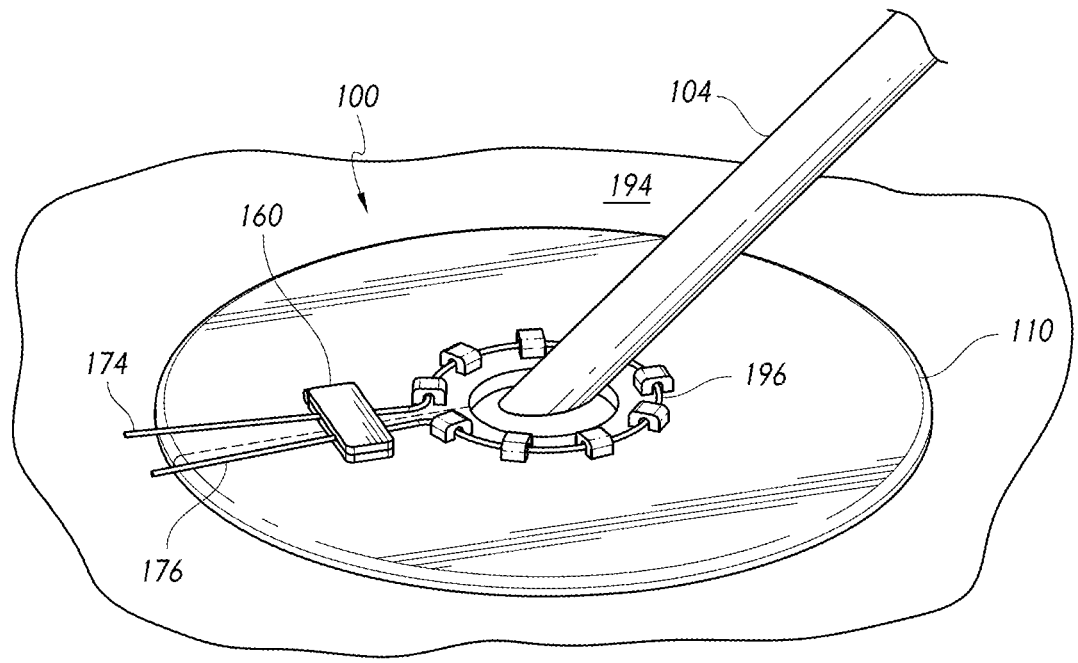

FIG. 7 shows the device 100 after the locking mechanism 120 has been mechanically coupled to the base 110. The tensioned section 196 provides cinching to pull most or all parts of the device 100, and the subject's skin to which it is attached, towards the device 104 to mechanically close (partially or completely) the gap or orifice 142 (FIG. 5) in the subject's tissue. The force/pressure can be periodically adjusted to keep the subject's tissue held snuggly against the outside of the device 104. The locking mechanism 120 can be locked and unlocked to adjust the forces/pressure applied to the subject.

Figure 8:
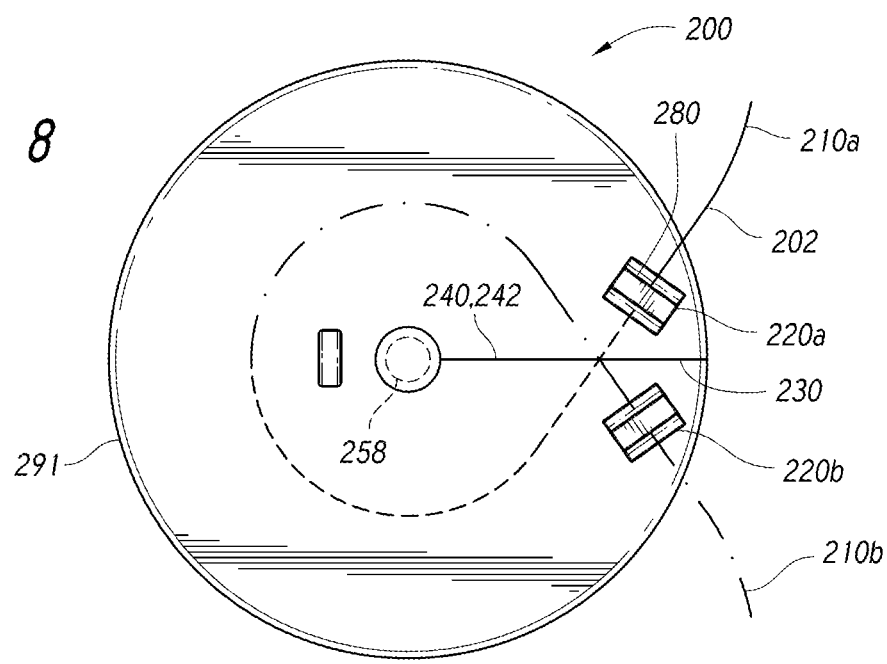
FIG. 8 is a plan view of a noninvasive cinching device in accordance with an embodiment of the technology.

FIGS. 8-26 show noninvasive devices and features that are generally similar to the device 100 and features discussed in connection with FIGS. 1-7. FIG. 8 is a plan view of a noninvasive cinching device 200 ("device 200") that can include a flexible tensioner 202 with ends 210a, 210b (collectively "ends 210") receivable by corresponding tensioner retainers 220a, 220b (collectively "retainers 220"). When the retainers 220a, 220b hold the ends 210a, 210b, the tensioner 202 can extend across an access feature in the form of a slit 230 to help inhibit or limit separation between edges 240, 242. When the tensioner 202 is at the desired tension, the ends 210a, 210b can be crossed and inserted into the corresponding retainers 220a, 220b.

The ends 210a, 210b can be visually different to conveniently match the ends 201a, 210b to the corresponding retainers 220a, 220b. In some embodiments, the color of the end 210a can be the same color as the retainer 220a, and the color of the end 210b can be the same color as the retainer 220b. In one embodiment, the tensioner 202 can have a first color section (shown in dashed-dot line) and a second color section (shown in dashed line) that is different from the first color section. For example, the first color section can be red and the second color section can be green. The ends 210a, 210b can have other markings or other visual indicators that correspond to visual indicators of the retainers 220. Exemplary retainers are discussed in connection with FIGS. 9-16.

Figure 9:
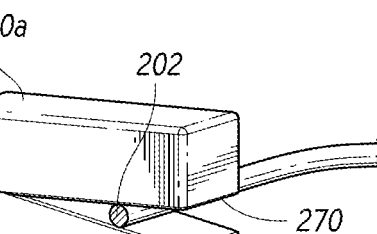
FIG. 9 is an isometric view of a tensioner retainer in accordance with an embodiment of the technology.
Figure 9:
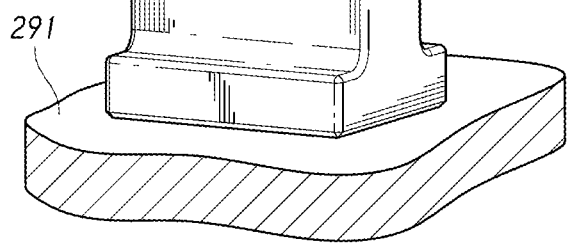
Figure 10:
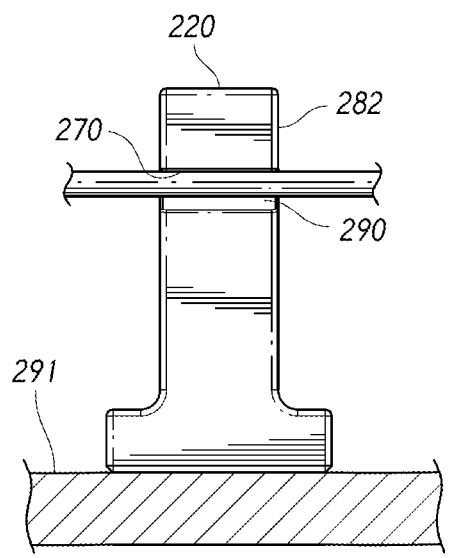
FIG. 10 is a side view of the tensioner retainer of FIG. 9.

FIG. 9 is an isometric view of the retainer 220a in accordance with one embodiment of the technology. FIG. 10 is a side view of the retainer 220a. The description of the retainer 220a applies equally to the retainer 220b. Referring now to FIG. 9, the retainer 220a can include a groove 270 dimensioned to receive the tensioner 202 (shown in cross section). The groove 270 can include an adhesive material, serrated surfaces, or other features that inhibit or prevent movement of the tensioner 202. Additionally or alternatively, the tensioner 202 may be ribbed, beaded, or knotted so as to lock in place when the tensioner 202 is inserted into the groove 270. In one embodiment, a knot (e.g., a square knot) can be formed along the tensioner 202. The tensioner 202 can be slid into the groove 270 to locate the knot on the back side 280 (FIG. 8) of the retainer 220a.

Figure 11:
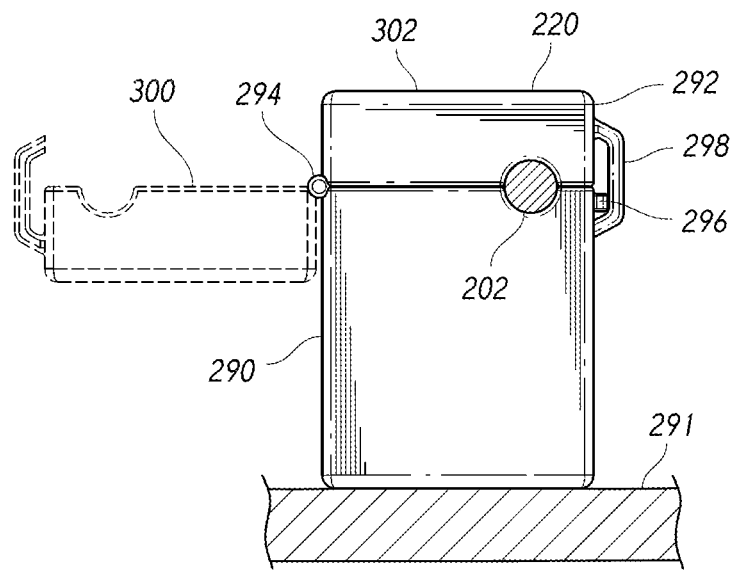
FIG. 11 is a front view of a tensioner retainer in accordance with an embodiment of the technology.
Figure 12:
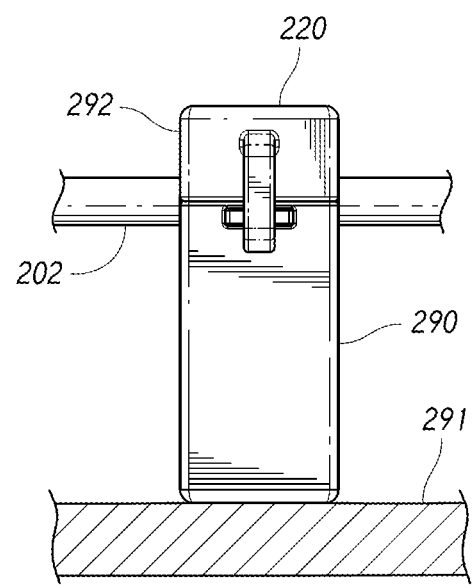
FIG. 12 is a side view of the tensioner retainer of FIG. 11.

FIGS. 11 and 12 are front and side views, respectively, of the retainer 220 in accordance with one embodiment of the present technology. Referring now to FIG. 11, the retainer 220 can include a main body 290, a cover 292, and a hinge 294. The main body 290 can be coupled to a base 291 (e.g., an adhesive pad) and includes a latch element 296. The cover 292 is rotatable between an open position 300 (shown in phantom line) and a closed position 302. As the cover 292 moves to the closed position 302, a latch 298 can engage the latch element 296 to lock the retainer 220. The latch 298 can be separated from the latch element 296 to unlock the retainer 220.

Figure 13:
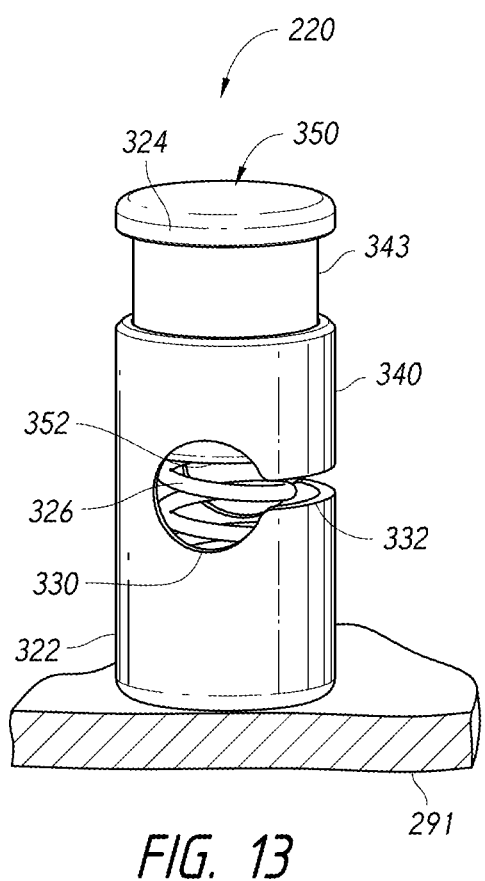
FIGS. 13 and 14 are front views of a tensioner retainer in accordance with an embodiment of the technology.
Figure 14:
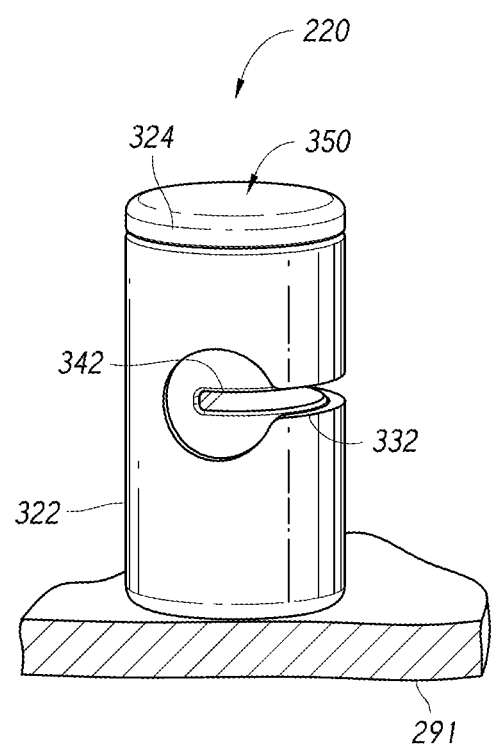

FIGS. 13 and 14 are front views of the retainer 220 in accordance with another embodiment of the present technology. The retainer 220 can be spring-loaded and can accommodate one or both ends of a tensioner and can allow for repeated cinching and un-cinching. When the spring-loaded retainer 220 is released, two inner surfaces can compress a tensioner, thus preventing relative movement of the tensioner, as discussed in connection with FIGS. 15 and 16.

Referring now to FIG. 13, the retainer 220 can include a retainer base 322, a locking element 324, and a biasing element 326. The retainer base 322 is coupled to the base 291 and includes a window 330 and a slot 332 extending between the window 330 and an outer surface 340. The biasing element 326 can include, without limitation, one or more springs (e.g., compression springs, helical springs, etc.) and can extend between a bottom surface 352 of a locking element body 343 and internal surface (not shown) of the retainer base 322. The locking element 324 can include a cap 350 and the locking element body 343 having a slot 342 (FIG. 14).

Figure 15:
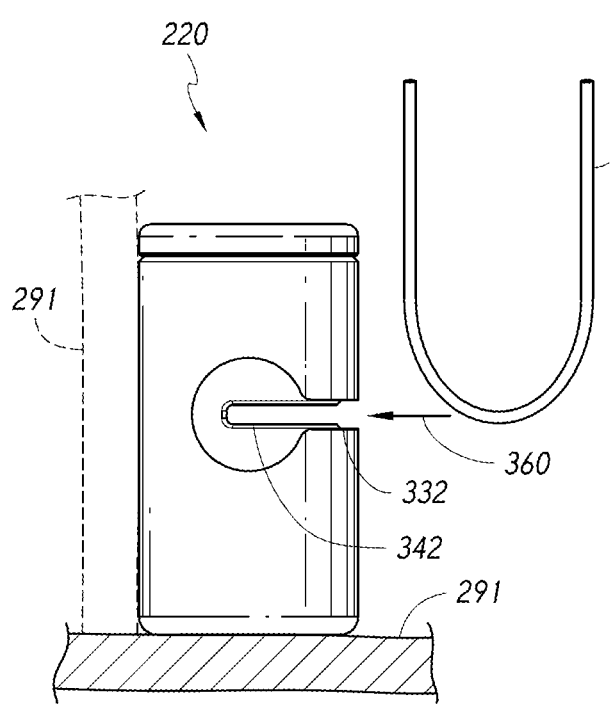
FIGS. 15 and 16 show a flexible tensioner being installed in the tensioner retainer.
Figure 16:
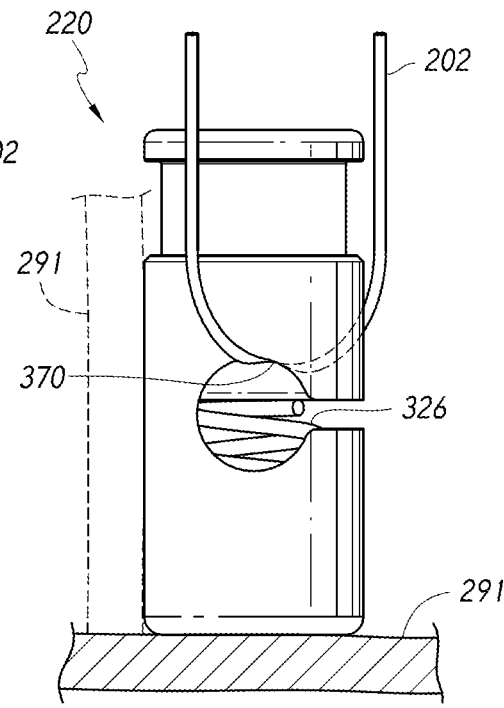

FIGS. 15 and 16 show one method of using the retainer 220. A user can press down on the locking element 324 to overcome the biasing force provided by the biasing element 326. After the slot 342 is aligned with the slot 332, the tensioner 202 can be inserted (indicated by arrow 360 in FIG. 15) through the slot 332 and into the slot 342. After the tensioner 202 is positioned within the slot 342, the user can allow the biasing member 326 to move the locking element 324 relative to the base 322 until the tensioner 202 is pinched by an edge 370 (FIG. 16) and the locking element 342.

The retainers (e.g., retainers 220 of FIG. 8) disclosed herein can also be in the form of cleats (e.g., boat-type cleats, dock type-cleats, etc.) about which end sections of the tensioner can be wrapped. Cleats may be used to shorten the lengths of free ends of the tensioner to prevent accidental entanglement of the tensioner with other external objects. In yet other embodiments, the retainers can be eliminated and the ends of the tensioner can be tied together. Additionally, orientations of the retainers can be selected to facilitate ease of use and/or comfort of the subject. For example, the base 291 of FIGS. 15 and 16 can be at the position illustrated in phantom line. The user can pinch opposite ends of the retainer 220 without applying appreciable pressure to the subject.

Figure 17:
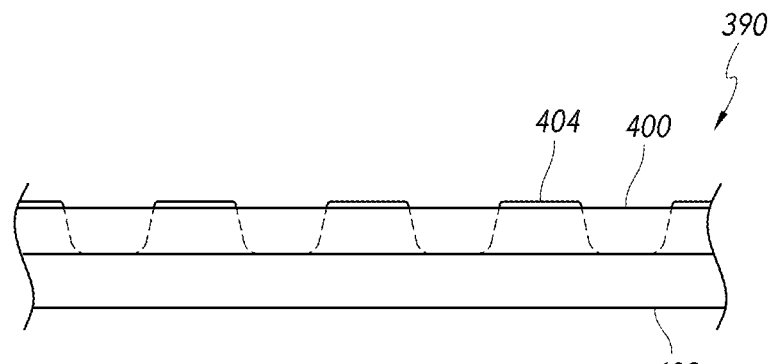
FIG. 17 is a side view of a base and a tensioner in accordance with an embodiment of the disclosure.
Figure 18:
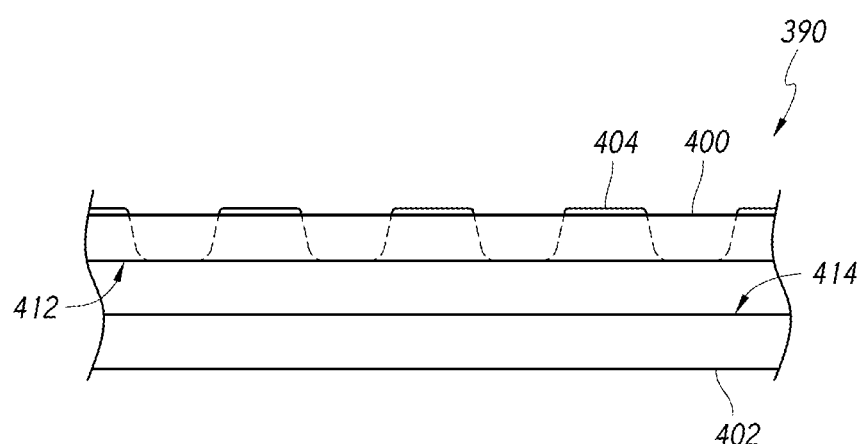
FIG. 18 is an exploded side view of the base of FIG. 17 in accordance with an embodiment of the technology.

FIG. 17 is a side view of a base 390 for a cinching device in accordance with an embodiment of the technology. FIG. 18 is an exploded side view of the base 390. Referring now to FIG. 17, the base 390 can have a multi-piece construction with an upper member 400 and a lower member 402. The upper member 400 can comprise, without limitation, one or more layers of the same or different materials and can be adhered, bonded, fused, or otherwise coupled to the lower member 402. The tensioner 404 can be laced through the upper member 400. Referring now to FIG. 18, sections of the tensioner 404 can be positioned between a lower surface 412 of the upper member 400 and an upper surface 414 of the lower member 402, which serves as a barrier to inhibit or prevent migration of bacteria and other contaminants across the layers of the base of the device. The characteristics of the members 400, 402 can be selected to have desired fluid permeability, air breathability, etc. In some embodiments, one or more layers of the base 390 include, in whole or in part, a fluid impermeable material, air permeable material, breathable material, barriers to microbial growth or transport through the base 390, or the like. The number and characteristics of the layers can be selected based on the desired overall characteristics of the base 390.

Figure 19:
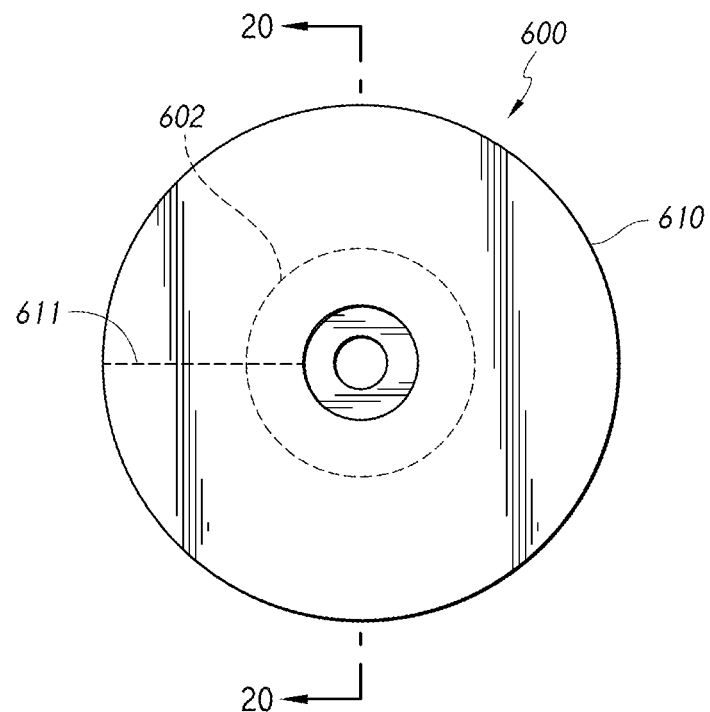
FIG. 19 is a plan view of a base for a cinching device in accordance with an embodiment of the technology.
Figure 20:
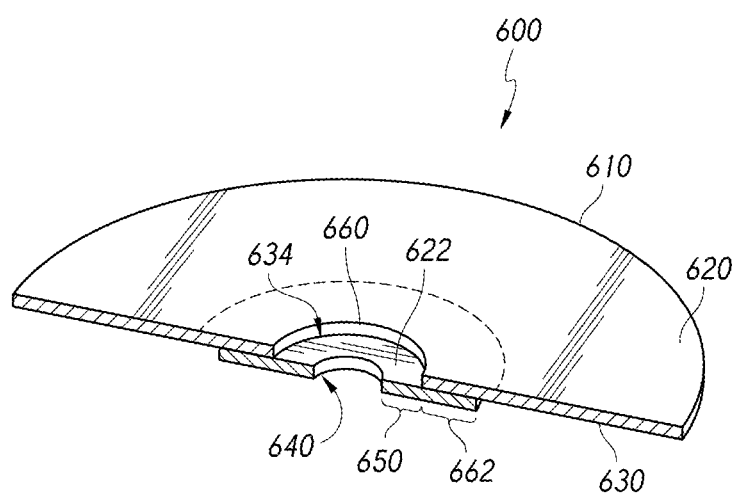
FIG. 20 is a cross-sectional view of the base taken along line 20-20 of FIG. 19.

FIG. 19 is a plan view of a noninvasive cinching device 600 ("device 600") in accordance with an embodiment of the present technology. FIG. 20 is a cross-sectional view of the device 600 taken along line 20-20 of FIG. 19. Referring now to FIG. 19, the device 600 can include a cinching assembly 602 (shown schematically in phantom line), a base 610, and an access feature 611. The cinching assembly 602 can include, without limitation, retainers (e.g., tensioner retainers, catheter retainers, instrument retainers, etc.), flexible tensioners, and other components disclosed herein. Referring now to FIG. 20, the base 610 can include a main body 620 and a cushion element 622. The main body 620 can include adhesive 630 and an opening 634. The cushion element 622 may serve as a comfort feature to prevent uncomfortable pinching of skin between the device 600 and a medical device extending through the base 610. The cushion element 622 can include a device-receiving opening 640, a cushioning section 650, and a mounting section 662. The mounting section 662 is physically coupled (e.g., adhered, bonded, fused, etc.) to the main body 620 such that the cushioning section 650 extends inwardly from an inner edge 660 of the main body 620. In one embodiment, the cushion element 622 is a patch with a monolayer or multilayer construction and can comprise cushioning material. The cushion element 622 may additionally or alternatively contain antibiotic substance(s), hemostatic substances, a desiccant, and/or fluid absorbing substances.

Figure 21:
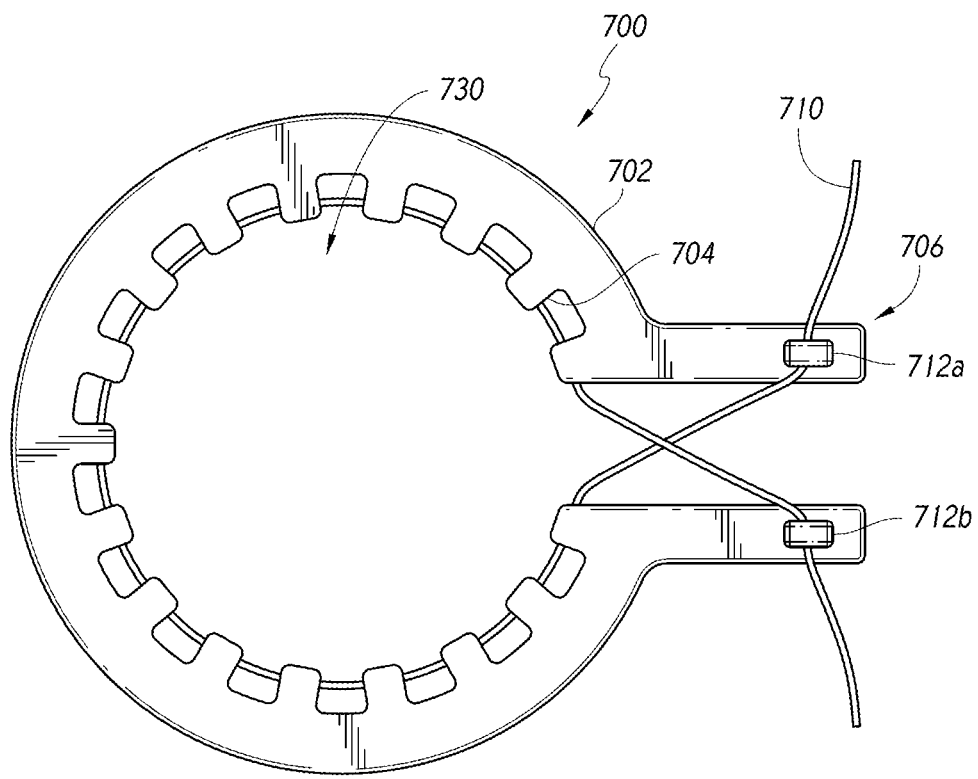
FIG. 21 is a plan view of a noninvasive cinching device in accordance with another embodiment of the technology.
Figure 22:
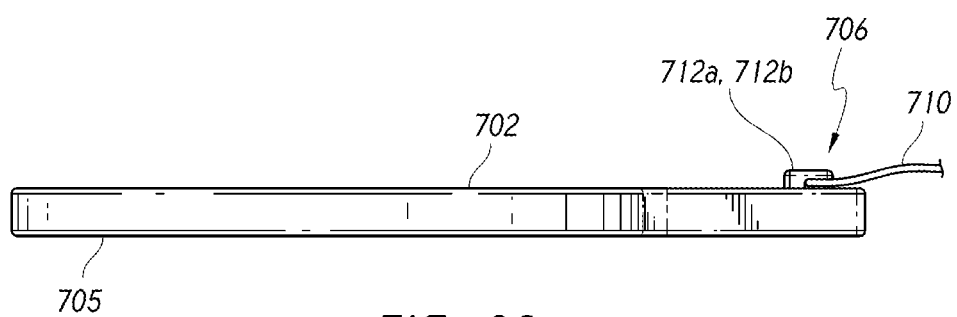
FIG. 22 is a side view of the cinching device of FIG. 21 in accordance with an embodiment of the technology.

FIG. 21 is a plan view of a noninvasive cinching device 700 ("device 700") in accordance with an embodiment of the present technology. FIG. 22 is a side view of the device 700 that can include a base 702 with an array of spaced apart holders 704 (one identified in FIG. 21) and adhesive 705 (FIG. 22). A cinching assembly 706 can include a tensioner 710 and retainers 712a, 712b (collectively "retainers 712"). The tensioner 710 is positioned circumferentially around the device's central opening 730 and is threaded through the series of holders 704. In some embodiments, each holder 704 is a tubular element through which the tensioner 710 can be slid. In other embodiments, each holder 704 can be partially or completely segmented rings, eyelets, or hooks through which the tensioner 710 passes. The holders 704 can be made, in whole or in part, of metal, plastic, cloth, wire, or durable material that can withstand forces applied during cinching.

Figure 23:
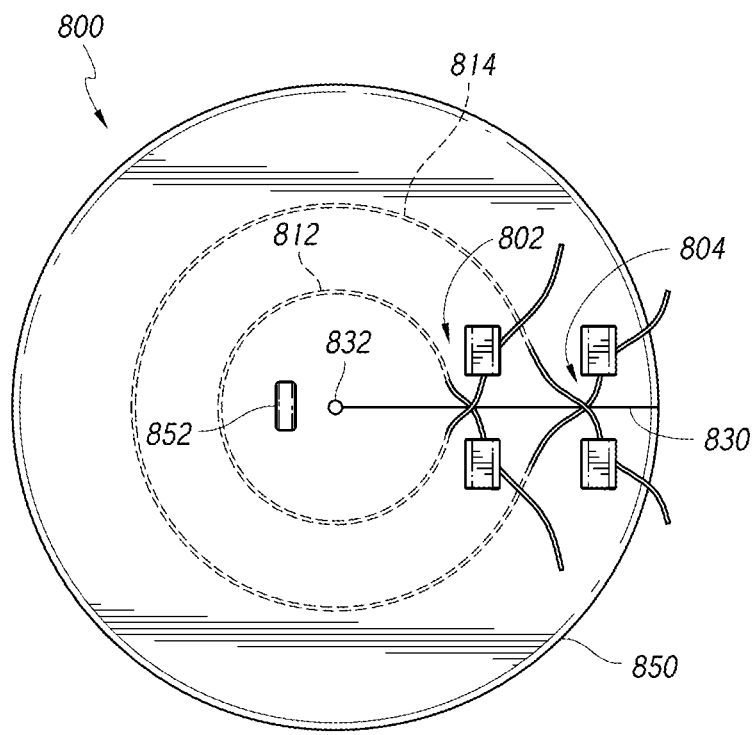
FIG. 23 is a plan view of a noninvasive cinching device with multiple cinching assemblies in accordance with an embodiment of the technology.

FIG. 23 is a plan view of a noninvasive cinching device 800 ("device 800") in accordance with embodiments of the present technology. The device 800 can include a plurality of cinching assemblies 802, 804. Each cinching assembly 802, 804 can be used to adjust the force applied to the subjects skin and can include, without limitation, circumferentially oriented holders (e.g., loops, hooks, eyelets, annular tubular member, etc.), one or more tensioners, and one or more tensioner retainers. A tensioner 812 (shown schematically in phantom line) of the cinching assembly 802 can be generally concentric with a tensioner 814 (shown schematically in phantom line) of the cinching assembly 804. A medical device can be moved through an access feature 830 and into a receiving opening 832 ("opening 832"). After the device is within the opening 832, one or both tensioners 812, 814 can be tensioned. Any of the cinching devices disclosed herein can have additional cinching assemblies for exerting additional force(s) to minimize, limit, or substantially prevent pericatheter bleeding, for example.

The device retainer 852 can couple the medical device to the base 850 and can include, without limitation, one or more clamps, adhesive members, or other elements suitable for releasably holding a medical device. For example, the cinching device 100 (FIGS. 1-7), cinching device 200 (FIG. 8), cinching device 600 (FIGS. 19 and 20), and cinching device 700 (FIGS. 21 and 22) can include one or more device retainers. For example, the cinching device 100 of FIG. 2 can have a device retainer for holding the catheter 104, and such device retainer can be similar to the retainers 220 discussed in connection with FIGS. 8-12.

Figure 24:
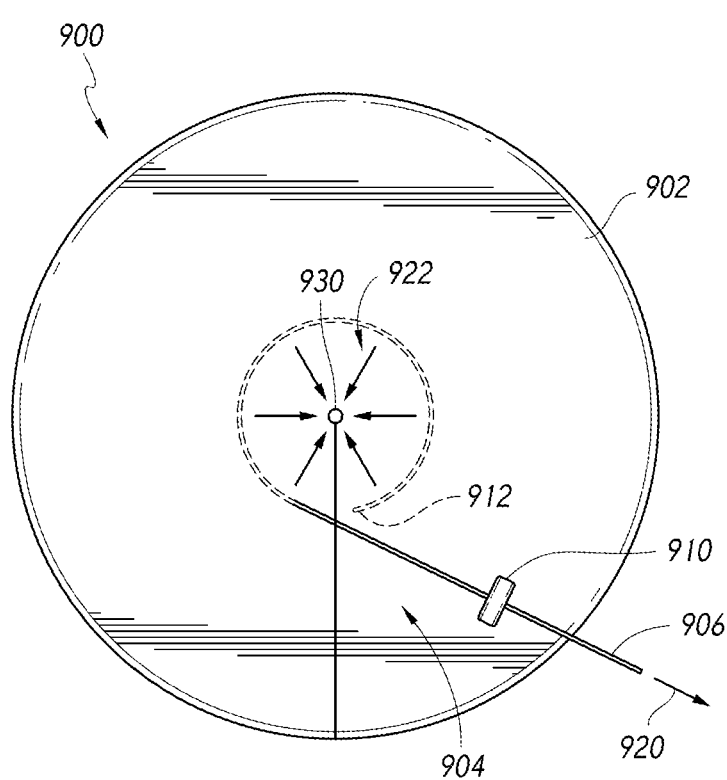
FIG. 24 is a plan view of a noninvasive cinching device with a tensioner fixedly coupled to a base in accordance with one embodiment of the technology.

FIG. 24 is a top plan view of a noninvasive device 900 ("device 900") in accordance with an embodiment of the technology. The device 900 can include a base 902 and a cinching assembly 904. The cinching assembly 904 can include a tensioner 906 and a tensioner retainer 910 coupled to the base 902. An end 912 of the tensioner 906 is physically coupled to the base 902. A section of the tensioner 906 shown in phantom line can extend through the base 902. In other embodiments, one or more holders can couple the tensioner 906 to the base 902. The user can pull the tensioner 906, as indicated by arrow 920, to draw the arcuate section the tensioner 906 inwardly, as indicated by arrows 922. The exposed section of the tensioner 906 can extend generally tangentially to the arcuate path along which the tensioner 906 extends about the opening 930.

Figure 25:
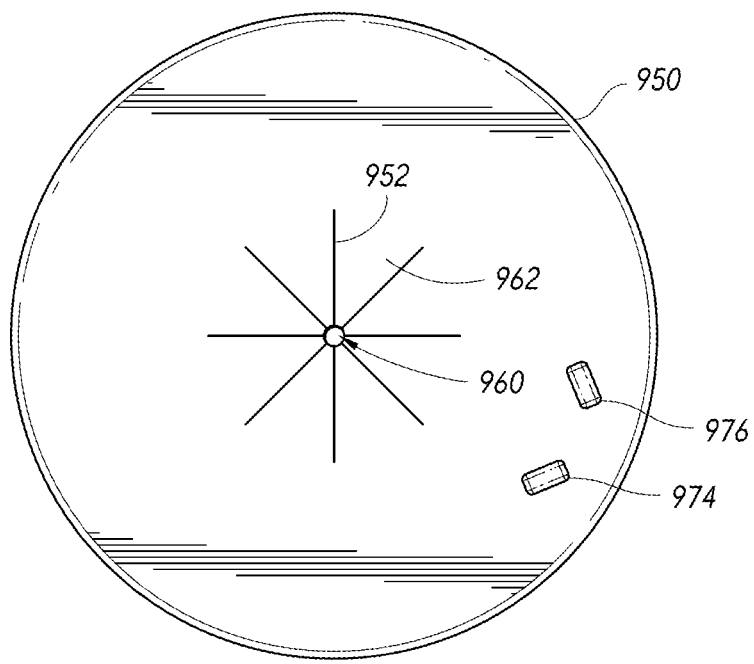
FIG. 25 is a plan view of a base of a cinching device in accordance with an embodiment of the technology.
Figure 26:
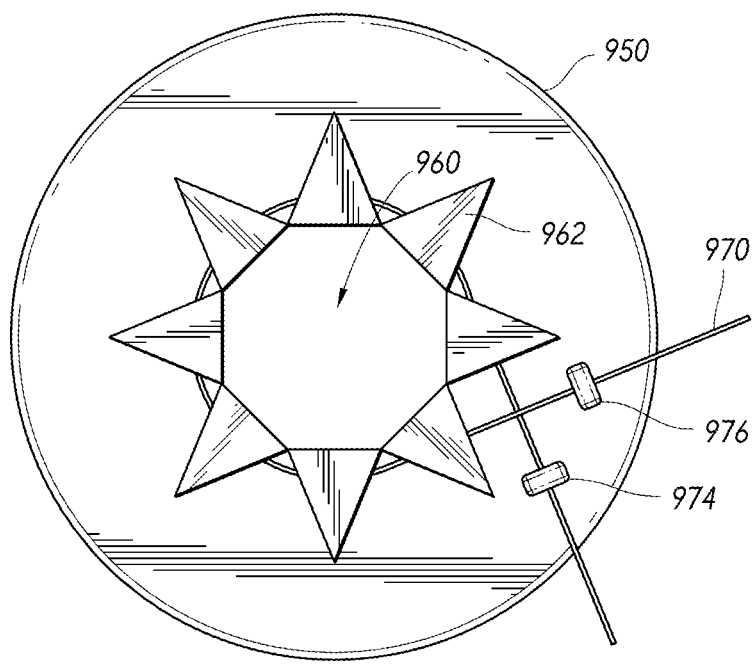
FIG. 26 is a plan view of the base of FIG. 25 and an installed tension.

FIG. 25 is a plan view of a base 950 for a cinching device in accordance with an embodiment of the technology. FIG. 26 is a plan view of the base 950 holding a tensioner. Referring now to FIG. 25, slits 952 (one identified) can extend from an opening 960. Flaps 962 (one identified) can be part of the base material and can be folded back or otherwise looped to accommodate the tensioner 970. FIG. 26 shows the tensioner 970 held by tensioner retainers 974, 976.

The above detailed descriptions of embodiments of the technology and examples are not intended to be exhaustive or to limit the technology to the precise form disclosed above. The devices disclosed herein can provide cinching that causes a mechanical closing or minimizing orifices. The mechanical cinching can cause the adherent surface, including skin, to be drawn inwardly towards an orifice to enhance diminution or stoppage of material flow through the orifice. When an instrument is positioned in the orifice, the cinching can push tissue surrounding the instrument towards the instrument, thereby closing (e.g., partially or completely closing) the orifice. The tension in the tensioner can be selectively increased or decreased to increase or decrease the cinching force applied to the subject's skin. The mechanical cinching may also allow for the occlusion and/or tamponade of the orifice. The size of the device can be selected based on the size and location of the orifice in the subject, the configuration of the instrument, if any, positioned in the orifice, and desired functionality. The desired functionality can include closing the orifice, closing or eliminating a gap between the instrument and the subject's skin, tamponading, or the like. Additional features can be coupled to or incorporate into the cinching device so as to impart additional functionality. These additional features can include, without limitation, additional adhesive properties to ensure proper hold of the device onto skin, additional absorbency of fluid from the skin, and a larger surface area barrier protect the wound from external sources. In some embodiments of the technology, a noninvasive closure device includes an adhesive pad 110 (FIG. 2) defining a catheter-receiving opening 160 (FIG. 2) and a means for applying inward pressure to a subject's skin to which the adhesive pad is attached to push the subject's tissue towards a catheter 140 (FIG. 2) through the catheter-receiving opening. The means for applying inward pressure includes a flexible elongate tensioner 130 (FIG. 2) configured to be spaced apart from and extend about the catheter-receiving opening 160 (FIG. 2) and a tensioner retainer 120 (FIG. 2) coupled to compliant adhesive pad and configured to receive the flexible elongate tensioner.

The catheter-receiving openings disclosed herein can be in the form of a slit that may bisect the entire adhesive base or may extend radially from the center to the edge of the adhesive base. Additionally, the base may be scored or have a weakened region to allow convenient opening of the slit. In one embodiment, a score line extends from a central catheter-receiving opening to the outer edge of the base such that a user can manually separate the base along the score line. In some embodiments, the base can include a plurality of score lines which the user can select to provide an access path to the catheter-receiving opening.

The devices disclosed herein can have dimensions selected to achieve desired forces. In some embodiments, the cinching devices disclosed herein can have diameters in a range of about 2 inches to about 5 inches (e.g., 2 inches, 2.75 inches, 4 inches), but other dimensions can be used. The applied forces can be adjusted to control or eliminate leaks. In some embodiments, the cinching devices can reduce a leak rate by 90%, 95%, 98%, or 99%. The cinching devices can reduce a 300 cc/hour leak rate to about zero (e.g., less than 1 cc/hour, less than 3 cc/hour, or less than 5 cc/hour). In another embodiment, the cinching devices can reduce a 10,000 cc/hour leak rate to a leak rate equal to or less than 120 cc/hour or less, for example.

Although specific embodiments of, and examples for, the technology are described above for illustrative purposes, various equivalent modifications are possible within the scope of the technology, as those skilled in the relevant art will recognize. While steps are presented in a given order, alternative embodiments may perform steps (including the steps discussed in connection with FIGS. 4-7) in a different order to treat a wide range of patients, including patients with renal failure, patients on anticoagulation regimen, patients with coagulopathy, patients undergoing venous thrombolysis, or the like. In some embodiments, the devices are used with percutaneous catheters (e.g., catheters inserted for surgical drainage or gastrostomy tubes), peritoneal dialysis catheters, feeding tubes, drains (e.g., abscess drains, nephrostomy and biliary drains, intraoperative surgically placed drains, etc.), or other instruments that may produce leakage. Additionally, the devices disclosed herein can be modified to provide a wide range of different force/pressure profiles and may not provide cinching action. Additional methods and devices are disclosed U.S. Provisional Patent Application No. 61/922,398 entitled "MEDICAL DEVICES AND METHODS FOR COVERING/CLOSING OPENINGS IN TISSUE" and U.S. Provisional Application Ser. No. 61/992,812 entitled MEDICAL DEVICES, DRESSINGS, AND METHODS FOR CLOSING OPENINGS IN TISSUE, which are incorporated herein by reference in their entireties.

Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded.

It will be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A noninvasive cinching device, comprising:
a compliant adhesive pad defining a catheter-receiving opening;
a flexible elongate tensioner configured to be coupled to the compliant adhesive pad such that a tensioned section of the flexible elongate tensioner is spaced apart from and extends about both the catheter-receiving opening and a catheter extending through the catheter-receiving opening;
a tensioner retainer configured to hold the flexible elongate tensioner; and
a plurality of spaced apart holders coupled to the compliant adhesive pad, wherein the holders are arranged in a discrete fashion and configured to move radially inward toward the catheter such that the compliant adhesive pad applies sufficient radially inward shear pressure to a subject's skin to substantially decrease a radial distance between a perimeter of the catheter-receiving opening and the catheter to press the subject's tissue toward the catheter when the catheter is positioned in the catheter-receiving opening, a region of the compliant adhesive pad surrounding the catheter-receiving opening lays flat along subject's skin, and the flexible elongate tensioner is held by the holders, thereby inhibiting pericatheter leakage.

2. The noninvasive cinching device of claim 1, wherein the flexible elongate tensioner extends along a circumferential path about the catheter-receiving opening such that the compliant adhesive pad exerts forces toward the catheter when the flexible elongate tensioner is tensioned.

3. The noninvasive cinching device as in any preceding claim, wherein the tensioner retainer is configured to securely hold the flexible elongate tensioner such that the flexible elongate tensioner provides radially inward forces that promote hemostasis at an exit site of the catheter when the flexible elongate tensioner is tensioned.

4. The noninvasive cinching device as in any preceding claim, wherein the compliant adhesive pad applies an inward pressure to the subject's tissue adjacent to the catheter-receiving opening when tension in the flexible elongate tensioner is increased and decreased.

5. The noninvasive cinching device as in any preceding claim, wherein the tensioner retainer has a closed configuration for securely holding the flexible elongate tensioner and an open configuration for receiving and/or releasing the flexible elongate tensioner.

6. The noninvasive cinching device as in any preceding claim, wherein the compliant adhesive pad holds the flexible elongate tensioner such that the flexible elongate tensioner encircles the catheter-receiving opening.

7. The noninvasive cinching device as in any preceding claim, wherein the flexible elongate tensioner is laced through the holders.

8. The noninvasive cinching device of claim 7, wherein the flexible elongate tensioner passes repeatedly through the holders.

9. The noninvasive cinching device as in any preceding claim, wherein the tensioner retainer has a closed configuration for securely holding the flexible elongate tensioner and an open configuration for releasing the flexible elongate tensioner, and the tensioner retainer has a biasing member that biases the tensioner retainer toward the closed configuration.

10. The noninvasive cinching device as in any preceding claim, wherein the compliant adhesive pad includes:
    an upper member; and
    a lower member with a lower surface comprising adhesive, wherein the lower member is located between the flexible elongate tensioner and the subject's skin when the adhesive is adhered to the subject's skin.

11. A noninvasive closure device, comprising:
    an adhesive pad defining a catheter-receiving opening; and
    a cinching assembly carried by the complaint adhesive pad and including a flexible tensioner and a plurality of spaced apart holders, the holders arranged in a discrete pattern and configured to move radially inward toward the catheter, wherein the cinching assembly has an unlocked configuration for adjusting tension in a section of the flexible tensioner at least partially encircling the catheter-receiving opening to selective increase or decrease inward pressure applied to a subject's tissue located between the compliant adhesive pad and a catheter positioned in the catheter-receiving opening and a locked configuration for maintaining tension in the section of the flexible tensioner held by the holders, thereby inhibiting pericatheter leakage.

12. The noninvasive closure device of claim 11, wherein the cinching assembly includes a retainer movable between an open configuration for receiving and/or releasing the tensioner and a closed configuration for holding the tensioner.

13. The noninvasive closure device as in one of claims 11-12, wherein at least a portion of the complaint adhesive pad extends radially inward from the section of the flexible tensioner when the flexible tensioner is tensioned to promote hemostasis.

14. The noninvasive closure device as in one of claims 11-13, wherein the holders are coupled to the complaint adhesive pad.

15. The noninvasive closure device as in one of claims 11-14, wherein a section of the flexible tensioner extends about an arcuate path defined by the cinching assembly when the flexible tensioner is tensioned to inhibit pericatheter leakage.

16. A method for inhibiting pericatheter leakage, the method comprising;
    adhering a conformable pad of a cinching device to a subject's skin such that the conformable pad surrounds a catheter extending from an exit site along the subject's skin; and
    tensioning a flexible elongate tensioner of the cinching device such that a section of the flexible elongate tensioner extending along an arcuate path about the catheter pulls the conformable pad, a plurality of holders coupled to the conformable pad and arranged in a discrete fashion, and the subject's skin inwardly to apply a generally uniform radially inward pressure to push the subject's tissue inward toward the exit site so as to inhibit pericatheter leakage, wherein tensioning the flexible elongate tensioner moves the plurality of holders radially inward.

17. The method of claim 16, wherein tensioning the flexible elongate tensioner includes pulling the flexible elongate tensioner to apply sufficient force to the subject's skin to inhibit pericatheter leakage.

18. The method as in one of claims 16-17, further comprising moving a tensioner retainer from an unlocked configuration for receiving the flexible elongate tensioner to a locked configuration for holding the flexible elongate tensioner.

19. The method as in one of claims 16-18, further comprising coupling the catheter to the conformable adhesive pad using a catheter clamp.

20. The method as in one of claims 16-19, wherein tensioning of the flexible elongate tensioner is sufficient to reduce a leak rate of body fluids at the exit site.

21. The method of claim 20, wherein tensioning the flexible elongate tensioner is sufficient to reduce the leak rate by at least about 90%.

22. The noninvasive cinching device of claim 1, wherein the compliant adhesive pad further comprises an access feature extending between an outer edge of the compliant adhesive pad and the catheter-receiving opening.

23. The noninvasive cinching device of claim 22, wherein a gap is formed between opposing ends along the access feature when the compliant adhesive pad is applied, and wherein the gap is configured to narrow when tension is applied to the flexible elongate tensioner.

* * * * *